US012376929B2

(12) United States Patent  
Shang et al.

(10) Patent No.: US 12,376,929 B2  
(45) Date of Patent: Aug. 5, 2025

(54) DRIVER MODULE

(71) Applicant: Precision Robotics Limited, London (GB)

(72) Inventors: Jianzhong Shang, London (GB); Etienne Francois Joseph Dondez, London (GB); Tamas Csaba Hernadi, London (GB)

(73) Assignee: PRECISION ROBOTICS LIMITED, London (GB)

( * ) Notice: Subject to any disclaimer, the term of this patent is extended or adjusted under 35 U.S.C. 154(b) by 649 days.

(21) Appl. No.: 17/642,103

(22) PCT Filed: Sep. 10, 2020

(86) PCT No.: PCT/GB2020/052179  
§ 371 (c)(1),  
(2) Date: Mar. 10, 2022

(87) PCT Pub. No.: WO2021/048548  
PCT Pub. Date: Mar. 18, 2021

(65) Prior Publication Data  
US 2022/0354605 A1  Nov. 10, 2022

(30) Foreign Application Priority Data  
Sep. 11, 2019 (GB) ..................... 1913118

(51) Int. Cl.  
*A61B 17/00* (2006.01)  
*A61B 34/00* (2016.01)  
*A61B 34/30* (2016.01)

(52) U.S. Cl.  
CPC .............. *A61B 34/71* (2016.02); *A61B 17/00* (2013.01); *A61B 2017/00323* (2013.01);  
(Continued)

(58) Field of Classification Search  
CPC ........... A61B 2017/00323; A61B 2017/00371; A61B 2017/00398; A61B 2017/00477;  
(Continued)

(56) References Cited

U.S. PATENT DOCUMENTS 4,278,304 A    7/1981  Traut  
2006/0199999 A1  9/2006  Ikeda et al.  
(Continued)

FOREIGN PATENT DOCUMENTS

CN    208301682 U     1/2019  
WO    2007146987 A2  12/2007  
(Continued)

OTHER PUBLICATIONS

Intentional Search Report from PCT Appl. No. PCT/GB2020/052179, dated Nov. 23, 2020.

*Primary Examiner* — Brian T Gedeon  
(74) *Attorney, Agent, or Firm* — HSML P.C.

(57) ABSTRACT

A driver module for actuating a tendon, the driver module comprising:
a slider comprising a base portion, a tendon receiving portion and a body portion, the tendon receiving portion being spaced apart from the base portion and the body portion extends from the base portion to the tendon receiving portion, the module further comprising a slider receiving portion having a first end and a second end and engageable with the base portion of the slider such that the slider is moveably attachable to the slider receiving portion.

18 Claims, 9 Drawing Sheets

(52) U.S. Cl.
CPC ............ *A61B 2017/00371* (2013.01); *A61B 2017/00398* (2013.01); *A61B 2017/00477* (2013.01); *A61B 2034/715* (2016.02)

(58) Field of Classification Search
CPC .......... A61B 2017/00367; A61B 17/00; A61B 34/71; A61B 34/30
See application file for complete search history.

(56) References Cited

U.S. PATENT DOCUMENTS

| | | |
|---|---|---|
| 2010/0256558 A1 | 10/2010 | Olson et al. |
| 2015/0265355 A1 | 9/2015 | Prestel et al. |
| 2019/0192245 A1 | 6/2019 | Abbott et al. |

FOREIGN PATENT DOCUMENTS

| | | |
|---|---|---|
| WO | 2015142290 A1 | 9/2015 |
| WO | 2017205333 A1 | 11/2017 |
| WO | 2018207136 A1 | 11/2018 |

DRIVER MODULE

CROSS-REFERENCE TO RELATED APPLICATIONS

This application is a National Phase application under 35 U.S.C. 371 of PCT/GB2020/052179, filed Sep. 10, 2020, and claims the benefit of and priority to GB Application No. 1913118.4, filed Sep. 11, 2019, the disclosures of which are hereby incorporated herein by reference in their entirety.

This invention relates to a driver module for actuating a tendon, and particularly, but not exclusively, to a driver module for use in driving the articulation of a surgical instrument through the actuation of a plurality of tendons. The tendons may operate antagonistically in pairs such that the actuation of a first tendon in the pair results in a corresponding but opposed actuation of a second tendon in the pair. The invention is particularly directed to a driver module for actuating a tendon, a surgical instrument comprising the driver module, a method of attaching tendons to a driver module while pre-tensioning the tendons and a method of removably fitting a driver module to a motor module.

Surgical operations require the making of an incision in order for the physician to access internal parts of the body. Minimally invasive surgeries are operations in which the size of the incision is limited to reduce the healing time, associated pain and risk of infection of the resulting wound. Minimally invasive surgeries are therefore preferable for the well-being of a patient. However, due to the reduced size of the incision, minimally invasive surgeries were initially restricted to relatively simple procedures.

In recent years a variety of surgical instruments has been developed to provide physicians with the ability to perform increasingly complex procedures as minimally invasive surgeries. Known surgical instruments comprise an end effector, such as mechanical forceps, graspers, a needle holder or scissors, that enable the performance of certain actions required in surgical procedures. The end effector may be coupled to an articulation portion of the surgical instrument which provides the end effector with a number of degrees of freedom, thus enabling the end effectors to perform complex manoeuvres necessary for surgical procedures. The articulation portion may then be coupled to a hollow shaft which allows the end effector to be positioned in a required part of the body. The shaft may in turn be coupled to a driver module of the surgical instrument which provides inputs that control the end effector and articulation portion. The overall surgical instrument is therefore able to perform relatively complex surgical techniques.

Known end effectors, articulation portions, shafts and combinations thereof are small in their maximum width or diameter, often less than 1 cm. However, these portions of known surgical instruments, and particularly the shaft, may extend over considerable lengths, often in excess of 15 cm. The narrow width and extended length of the surgical instrument enable surgical techniques to be performed as minimally invasive procedures.

Known surgical instruments such as that described above are of great benefit to surgical operations as they allow relatively complex surgical techniques to be performed in a minimally invasive way.

However, there are issues with known surgical instruments of the type described above.

The end effector and articulating portion of a known surgical instrument require articulation by a means that does not impact on the small size of the components. A known method of achieving this is to attach first ends of tendons to different parts of the end effector and articulation portion. The tendons then extend through the hollow shaft and second ends of the tendons are attached to some form of actuator in the driver module of the surgical instrument. Actuation of the tendons provides articulation of the end effector and articulation portion.

Known driver modules are complex because they comprise a large number of moving parts in order to actuate the tendons with great precision.

Known driver modules are also expensive. The complexity and number of the parts required result in a high overall cost of manufacturing the driver modules. Due to the expense of the driver modules, they are required to be used more than once in order to make them cost efficient. This results in issues relating to sterility as it is crucial that any portion of the surgical instrument, which may come in to contact with the patient, is sterile.

Known driver modules suffer from an issue referred to as 'backlash'. When a tendon is actuated, the portion of the surgical instrument the tendon is attached to moves in response to the tendon's actuation. In known driver modules it is possible that the momentum provided by the actuation of the tendon is not halted when the tendon stops moving because the tendon is flexible. As a result the relevant part of the surgical instrument may continue to move, despite the actuation of the tendon having stopped. The relevant part of the surgical instrument is therefore in a different position to that it is intended to be in.

Backlash has two negative implications. The first is that the physician controlling the surgical instrument may not have a clear view of the surgical instrument, if any view at all, therefore it is important that the surgical instrument is in exactly the position it is intended to be in, otherwise harm could be caused to the patient. The second implication is that when the physician comes to control the relevant part of the surgical instrument again through a new actuation of the tendon, there may be a period of 'lag' between actuation of the tendon and movement of the relevant part. In other words a certain amount of actuation of the tendon may be performed before the relevant part starts to move. This is due to the tendon needing to be tensioned again before it is able to impart force on the relevant part. Again, this results in the surgical instrument acting differently to what the controlling physician is expecting, which may result in unintentional movement of the surgical instrument that may harm the patient.

According to a first aspect of the invention there is provided a driver module for actuating a tendon, the driver module comprising:
  a slider comprising a base portion, a tendon receiving portion and a body portion, the tendon receiving portion being spaced apart from the base portion and the body portion and extending from the base portion to the tendon receiving portion, the module further comprising a slider receiving portion having a first end and a second end and engageable with the base portion of the slider such that the slider is moveably attachable to the slider receiving portion.

By means of the present invention, a tendon may be actuated through movement of the slider. Because the base portion of the slider, which is engageable in a slider receiving portion, is spaced apart from the tendon receiving portion by means of the body portion, the tendon receiving portion may be aligned with a tendon to be controlled with the slider. At the same time, the base portion may be suitably positioned to engage with a slider receiving portion to allow movement of the slider.

This may be advantageous when the driver module forms part of a surgical instrument comprising a shaft through which tendons extend in order to operate the surgical instrument. In such embodiments of the invention, the tendons may be readily received by the tendon receiving portion of the slider without the need to divert the tendon. This obviates the need for further components such as pulleys in order to appropriately direct the tendon.

In such embodiments, the tendon receiving portion may receive an end of a tendon that extends along a shaft and exits the shaft receiving portion. The end of the tendon may further be fixed to the tendon receiving portion by any suitable means such as crimping, glue or solder. For example, in some embodiments of the invention the tendon receiving portion may, itself, be crimped around the tendon in order to hold the received end of the tendon in place within the tendon receiving portion.

In embodiments of the invention the driver module comprises a shaft receiving portion positioned towards the first end of the slider receiving portion, wherein the tendon receiving portion is aligned with the shaft receiving portion.

In such embodiments of the invention, a tendon extending along a shaft may exit the shaft and be received by the tendon receiving portion without having to be significantly diverted.

In embodiments of the invention the body portion of the slider further comprises an alignment portion, the alignment portion being adapted to position the tendon receiving portion of the slider in alignment with the shaft aperture.

In such embodiments of the invention, the base portion of the slider may be engageable with the slider receiving portion in a position that is not aligned with the shaft aperture. The alignment portion may therefore extend from the base portion and, at least partially, across a space between the slider receiving portion and the shaft aperture to provide alignment of the tendon receiving portion with the shaft aperture.

In embodiments of the invention, the slider comprises a drive portion extending from the base portion such that the base portion is positioned between the body portion and the drive portion.

In such embodiments of the invention, the drive portion of the slider may extend away from the body portion and away from the base portion of the slider. Such an arrangement may lead to a more efficient design of the drive module since the drive portion of the slider will not interfere with the tendon receiving portion of the slider.

In embodiments of the invention, the slider receiving portion comprises a channel extending at least partially along the length of the slider receiving portion between the first end and the second end, the channel being adapted to receive the base portion of the slider, whereby the base portion is slideably moveable within the channel.

In embodiments of the invention, the channel is linear, although in other embodiments of the invention the channel may be curved, for example.

In embodiments of the invention, the channel is adapted to receive the base portion of the slider such that the base portion is slidably moveable within the channel. In other words, movement of the slider is constrained by the dimensions of the channel and is generally linear movement, although as explained above the movement could also follow a curved trajectory.

In embodiments of the invention, the channel may extend substantially from the first end of the slider receiving portion to the second end of the slider receiving portion. However, in other embodiments of the invention, the channel extends partially along the length of the slider receiving portion.

The driver module may further comprise a first roller having an axis, and configured to be axially rotatable, the first roller being positionable such that the axis of the first roller is normal to the base portion of the slider and engageable with the base portion of the slider such that the movement of the slider causes axial rotation of the first roller.

In such embodiments of the invention, the first roller will provide support to the slider when the slider moves along the slider receiving portion. This can help to minimise friction during movement of the slider.

The driver module may further comprise a second roller having an axis, and configured to be axially rotatable, the first and second rollers being spaced apart from one another, the first roller being engageable with the first side of the base portion, and the second roller being engageable with the second side of the base portion.

In such embodiments of the invention, a slider is supported at a first end and second end during movement within the slider receiving portion.

This can provide additional support and further reduce friction during movement of the slider.

In embodiments of the invention, the driver module further comprises a pre-tensioning actuator, the pre-tensioning actuator being moveable between a first position and a second position, wherein, in the first position the pre-tensioning actuator is engaged with the slider such that the slider is positioned towards the second end of the slider receiving portion, and wherein in the second position the pre-tensioning actuator is disengaged with the slider, the driver module further comprising a bias for biasing the pre-tensioning actuator towards the first position.

In such embodiments, with the pre-tensioning actuator in the first position the slider is moved toward the second end of the slider receiving portion, away from the shaft receiving portion. Therefore, a tendon (extending along a shaft, exiting the shaft and received by the tendon receiving portion of the slider) may be held in tension by the slider as the pre-tensioning actuator is biased towards moving the slider away from the shaft receiving portion and associated shaft. This is advantageous when the surgical instrument is not being used as maintaining tension within the tendon helps keep the tendon in good condition.

Alternatively, when the pre-tensioning actuator is in the second position, the slider is able to move freely up and down the slider receiving channel which is advantageous when the surgical instrument is being used as the slider does not experience any resistance to movement that might negatively affect its actuation of the tendon.

In embodiments of the invention, the driver module further comprises a deactivating device engageable with the pre-tensioning actuator and moveable to a deactivating position, wherein the pre-tensioning actuator is configured to its second position.

In such embodiments, when the driver module is to be used, the deactivating device may be moved to its deactivating position hence configuring the pre-tensioning actuator to its second position to enable free movement of the slider. Movement of the deactivating device to its deactivating position may be achieved inherently when the driver module is engaged with a barrier in preparation to use the surgical instrument.

In embodiments of the invention, the driver module comprises a plurality of sliders, each of which sliders is engageable with the slider receiving portion.

In such embodiments of the invention, the slider receiving portion comprises a plurality of channels spaced apart from one another each of which channels being engageable with one of the sliders.

In such embodiments of the invention, each slider will be engageable with one of the plurality of channels.

By means of the present invention, a plurality of tendons may be actuated through movement of the plurality of sliders. Further, the plurality of tendons may include a pair of tendons coupled to one another such that the pair of tendons act antagonistically to one another. In other words, if one of the pair of tendons is pulled in one direction then the other of the pair of tendons is consequently pulled in the opposite direction.

Therefore, in some embodiments, each of a pair of antagonistic tendons may be attached to a respective one of the plurality of sliders. A first of the sliders may be actuated in a first direction, thereby pulling its respective tendon in the first direction. This in turn causes the paired tendon to travel in a second direction opposite to the first direction and thereby pull a second slider attached to it in the second direction. Hence, pairs of the plurality of sliders may work antagonistically to one another by actuating antagonistic pairs of tendons.

In embodiments of the invention each channel will be associated with a single slider only. This means that in embodiments of the invention comprising a plurality of sliders, each slider is moveable within its own channel.

The channels may be linear although in other embodiments of the invention they may be curved.

In such embodiments of the invention, each slider may comprise a body portion comprising an alignment portion, the alignment portion being adapted to position the tendon receiving portion of the respective slider such that it is aligned with the shaft aperture. Accordingly a plurality of tendons may extend along the shaft of the driver module and each tendon may exit the shaft and be received by a respective tendon receiving portion without any of the tendons having to be significantly diverted from the axis of the shaft.

This means that it is not necessary to use extra components such as pulleys in order to appropriately route a tendon exiting from the shaft aperture in order for that tendon to reach its respective tendon receiving portion.

In embodiments of the invention, the body portion of each slider comprises a head portion positionable such that the head portion of that slider is abuttable with the head portion of at least one other adjacent slider.

In such embodiments of the invention, the tendon receiving portions of each of the sliders abut with or are close to adjacent sliders such that tendons exiting from a shaft aperture may be readily received by a respective tendon receiving portion without having to be diverted in order to reach that tendon receiving portion. Further, the sliders may lean against one another such that each slider is supported the other sliders adjacent to it. This may reduce the effect of any forces acting on a single slider, in use, and improve the durability of the sliders against bending or breaking.

In embodiments of the invention, the driver module may further comprise an attachment interface and a locking mechanism, the attachment interface being engageable with a mating interface, the locking mechanism being adapted to lock and unlock the attachment interface in engagement with the mating interface.

In such embodiments of the invention, the mating interface may be a mating interface forming part of a motor module for actuating the sliders of the driver module, or a barrier for providing a sterility barrier between the driver module and a motor module.

In embodiments of the invention, the locking mechanism comprises a latch comprising a wedge; which latch is moveable between a first position in which the wedge is received within the attachment interface, and a second position in which the wedge protrudes from the attachment interface; wherein the latch is biased towards the second position.

In such embodiments of the invention, when the attachment interface is engaged with a mating interface, the wedge may be engageable with a latch socket forming part of a barrier or motor module, for example. Engagement of the wedge with the latch socket may lock the attachment interface into engagement with the mating interface, thereby locking the driver module in engagement with the barrier or motor module, for example.

In embodiments of the invention, the drive module may further comprise a gear assembly, the gear assembly comprising a gear slider moveable in a linear direction, a gear wheel rotatable about a gear axis and a geared shaft rotatable about a shaft axis; the gear slider being engageable with the gear wheel, and the gear wheel being engageable with the geared shaft such that linear movement of the linear slider drives rotation of the gear wheel about the gear axis whereby the geared shaft rotates about the shaft axis.

In such embodiments of the invention, the geared shaft may be attachable to, or form part of, a shaft of a surgical instrument. The gear assembly may therefore be used to translate linear movement of an actuator forming part of a motor module; for example, to rotational movement of the shaft of the surgical instrument.

According to a second aspect of the present invention there is provided a surgical instrument comprising a driver module according to embodiments of the invention comprising a single slider, and further comprising a tendon, receivable at a first end by the tendon receiving portion of the slider;
- an articulation module, operably connectable to the tendon;
- a shaft extending from the driver module to the articulation module, wherein the tendon extending through the shaft;
- an end effector, operably connected to the tendon; and
- a motor module, comprising an actuator, which actuator moveable and operatively engageable with the slider such that movement of the actuator causes movement of the slider.

According to a further aspect of the present invention there is provided a surgical instrument comprising a driver module according embodiments of the invention comprising a plurality of sliders and further comprising a plurality of tendons, each of the tendons being receivable at a first end by a tendon receiving portion of one of the plurality of sliders;
- a shaft, extending from the driver module, the plurality of tendons extending through the shaft;
- an articulation module operatively coupled to the shaft attachable to one or more of the tendons at a second end thereof;
- an end effector operatively coupled to the articulation module, and attachable to one or more of the tendons at a second end thereof; and a motor module comprising a plurality of actuators, each of the actuators being moveable and engageable with the plurality of sliders such that movement of the actuators provides movement of one of the plurality of sliders.

In embodiments of the invention the surgical instrument further comprises a barrier having a first side and a second side, the first side being engageable with the driver module and the second side being engageable with the motor module.

In such embodiments, prior to the barrier being provided to the surgical instrument for use, the barrier is sterile along all sides. However, in use, the second side is engaged with the motor module, which is non-sterile, therefore the second side of the barrier becomes non-sterile while the first side remains sterile as it is protected by the barrier and does not come into contact with non-sterile components. This means that the motor-module, which may be expensive, does not require sterilising after each use. This may be useful because the motor module may comprise various electrical components that could be damaged during sterilisation.

In embodiments of the invention the barrier comprises a plurality of barrier sliders, each of which barrier sliders comprises a first portion and a second portion, the first portion being engageable with one of the plurality of sliders of the driver module and the second portion being engageable with one of the plurality of actuators of the motor module.

In such embodiments, prior to the barrier being provided to the surgical instrument for use, all portions of the plurality of barrier sliders are sterile. In use, the second portion of each barrier slider may become non-sterile following engagement with one of the plurality of actuators of the motor module which is non-sterile. However, the first portion remains sterile as it is protected by the barrier. This again means that the motor-module does not require sterilising after each use. This may be useful because the motor module may comprise various electrical components that could be damaged during sterilisation.

In embodiments of the invention the mating interface is a barrier interface forming part of the first side of the barrier and comprises a latch socket in which the wedge is receivable when the attachment interface is engaged with the barrier interface, and the wedge is adapted such that, when the attachment interface is engaged with the barrier interface, the bias of the latch towards the second position causes the driver module to be biased towards a position in which the plurality of sliders engage with the plurality of barrier sliders and the plurality of tendons are tensioned.

In such embodiments of the invention, the wedge may be adapted, with a tapered shape for example, such that as it moves towards the second position (to which it is biased) it causes the attachment interface to move over the barrier interface until each of the plurality of sliders contacts a respective barrier slider. This may bring the tendon, attached to each slider, under tension and reduce backlash in the surgical instrument. Accordingly, the wedge may be adapted to cause optimal engagement of the attachment interface with the barrier interface.

The invention will now be described by way of example only with reference to the accompanying drawings in which.

Figure 1:
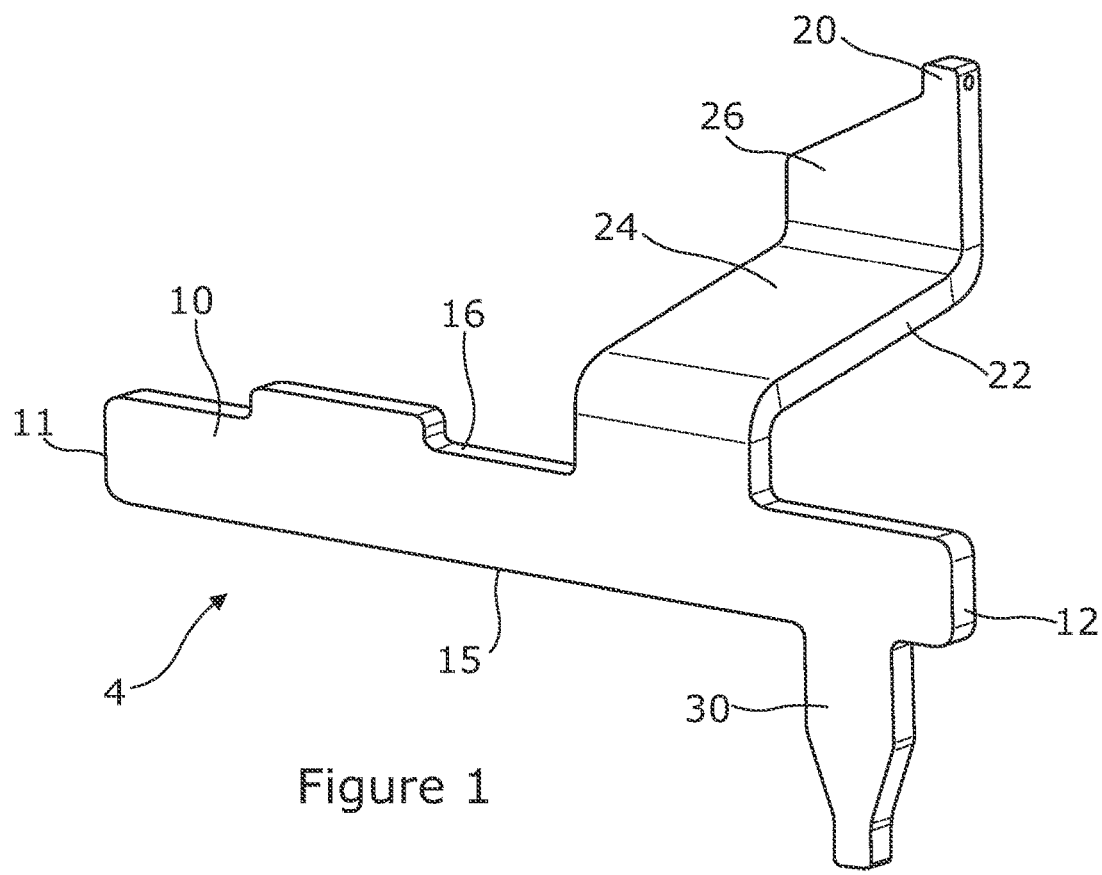
FIG. 1 is an illustration of a slider, according to an embodiment of a first aspect of the invention, comprising a base portion and a tendon receiving portion and a body portion.

Referring initially to FIG. 1, a slider according to an embodiment of the first aspect of the invention is designated generally by the reference numeral 4. The slider 4 comprises a base portion 10 and a tendon receiving portion 20 that is spaced apart from the base portion 10. The base portion 10 comprises a first end 11, a second end 12, a first side 15 and a second side 16.

The slider further comprises a body portion 22 extending from the base portion 10 to the tendon receiving portion 20, and a drive portion 30. The base portion 10 is positioned between the body portion 22 and the drive portion 30. The body portion 22 comprises an alignment portion 24 and a head portion 26.

Figure 2:
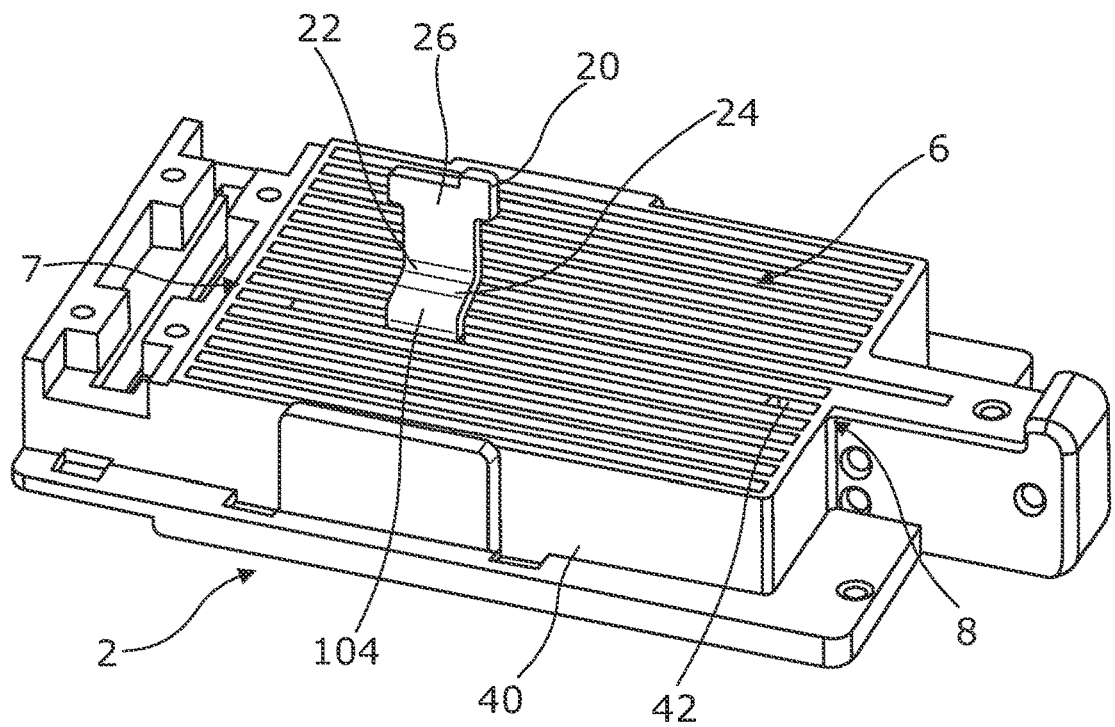
FIG. 2 is an illustration of a driver module, according to another embodiment of the first aspect of the invention, comprising a slider similar to that shown in FIG. 1 and a slider receiving portion.

Referring now to FIG. 2, a driver module according to another embodiment of the first aspect of the invention is defined generally by the reference numeral 2. The driver module 2 comprises a slider 104, and a slider receiving portion 6. The slider 104 is similar to and interchangeable with the slider 4 shown in FIG. 1. All of the features of slider 104 correspond to similar or identical features in slider 4, therefore for ease of reference the reference numerals used for slider 4 are also applicable to slider 104.

The slider receiving portion 6 comprises a first end 7 and a second end 8. The slider receiving portion 6 is engageable with the base portion 10 of the slider 104 such that the slider 104 is movably attachable to the slider receiving portion 6.

The driver module 2 further comprises a guide tray 40 comprising the slider receiving portion 6. The slider receiving portion 6 comprises a plurality of channels 42, each extending along the length of the slide receiving portion. In this embodiment of the invention, however, one channel 42 only is required to engage with the slider 4. The channel 42 is adapted to receive the base portion 10 of the slider 104 such that it is moveable along the channel 42. In some embodiments of the invention the slider receiving portion 6 may comprise a single channel 42 only. In this embodiment of the invention the channel 42 is linear, although in other embodiments of the invention it may follow a different trajectory.

Figure 3:
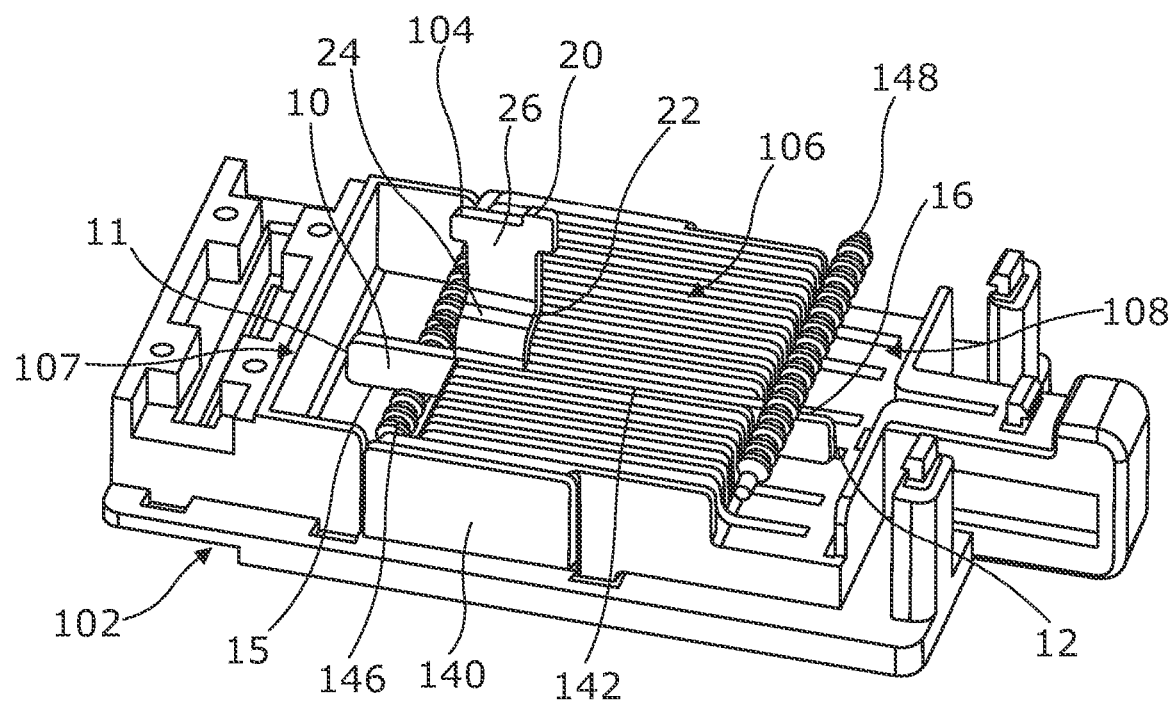
FIG. 3 is an illustration of a driver module, according to a further embodiment of the first aspect of the invention, this embodiment comprising a first roller and a second roller.

Referring now to FIG. 3, a driver module according to a further embodiment of the first aspect of the invention is defined generally by the reference numeral 102. The driver module 102 comprises the slider 104, and a slider receiving portion 106. The slider receiving portion 106 comprises a first end 107 and a second end 108. The slider receiving portion 106 is engageable with the base portion 10 of the slider 104 such that the slider 104 is movably attachable to the slider receiving portion 6.

The driver module 102 further comprises a guide tray 140, the guide tray 140 comprising the slider receiving portion 106. The slider receiving portion 106 comprises a plurality of channels 142, similarly to the embodiment of the invention shown in FIG. 2.

The driver module 102 further comprises a first roller 146 and a second roller 148 that are spaced apart from one another. Both the first roller 146 and the second roller 148 are engageable with the base portion 10 of the slider 4. The first roller is positioned to engage the slider 104 from the first side 15 of the base portion 10 and close to the first end 11, The second roller is positioned to engage with the slider 104 from the second side 16 of the base portion 10 and close to the second end 12.

The respective positions of the first roller 146 and the second roller 148 mean that, in use, the slider 104 remains engaged within the slider receiving portion 106. The first and second rollers 146, 148 are rotatable about their respective axes to facilitate the movement of the slider 104 toward and away from the first end 107 of the slider receiving portion 106.

In other words, linear movement of the slider 104 is translated to rotational movement of the first and second rollers 146, 148. Where the linear movement of the slider may otherwise have resulted in a sliding friction between the slider 104 and any contacting surfaces, in this embodiment of the invention at least some of the contact pressure that the slider exhibits in use is transferred from the slider 104 to the first and second rollers 146, 148. The first and second rollers 146, 148 may be configured to experience minimal friction when rotating about their respective axes. Therefore when, in use, the slider 104 is moved toward or away from the first end 107, the movement is facilitated by the first and second rollers 146, 148 with minimal friction.

Figure 4:
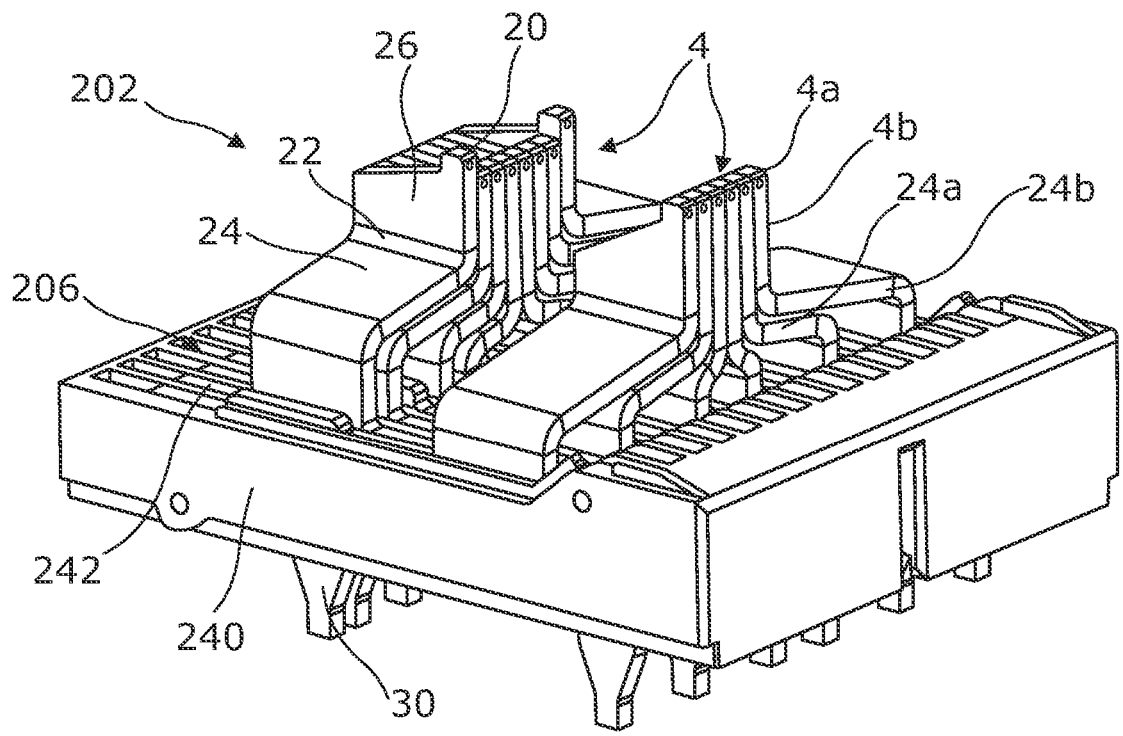
FIG. 4 is an illustration of a driver module according to a further embodiment of the first aspect of the invention, comprising a plurality of sliders.

Referring now to FIG. 4, a driver module according to another embodiment of the first aspect of the invention is defined generally by the reference numeral 202. The driver module 202 comprises a plurality of sliders 4 and a slider receiving portion 206. The slider receiving portion 206 is engageable with the base portion 10 of each of the plurality of sliders 4 such that each slider 4 is movably attachable to the slider receiving portion 206.

The driver module 202 further comprises a guide tray 240, the guide tray 240 comprising the slider receiving portion 206. The slider receiving portion 206 comprises a plurality of linear channels 242 that are spaced evenly across the guide tray 240. Each of the plurality of linear channels 242 is adapted to receive the base portion 10 of a corresponding slider 4 such that the base portion 10 of each slider 4 is moveable along the corresponding linear channel 242.

The alignment portion 24 of each of the plurality of sliders 4 is adapted to place the tendon receiving portions 20 of each slider 4 into close alignment with one another. In order to achieve this, the alignment portion 24 of each slider 4 is configured depending on the position of the corresponding channel 242 with which the slider 4 is engageable. As a result, a first slider 4a has an alignment portion 24a which has a different size and or shape to an alignment portion 24b of a second slider 4b. There is variance in the shape of the alignment portions 24 across each of the plurality of sliders 4. In embodiments of the invention, the shape of the alignment portions 24 may vary due to changes in their length, angle, orientation or any combination thereof. In other embodiments of the invention the shape of the alignment portions 24 may vary due to substantially differing geometries. In other embodiments of the invention the shape of the alignment portions 24 may not vary.

The alignment portion 24 of each slider 4 is further adapted to cause the head portion 26 of each slider to be positioned in close proximity with, or in abutment with the head portion 26 of at least one other adjacent slider 4 of the plurality of sliders.

In the embodiment shown in FIG. 4 adjacent head portions 26 abut with one another. The head portion 26 of each slider 4 is adapted to slideably abut with the head portion 26 of at least one adjacent slider 4 of the plurality of sliders 205. The sliders 4 are thus able to slide past one another whilst also abutting at least one adjacent slider. The abutment of the head portions 26 against one another provides the sliders 4 with support from the other sliders 4. This support is substantially normal to the direction of the plurality of linear channels 244 and normal to the base portion 10 of each of the plurality of sliders 205. The provision of support in this direction protects the sliders 4 from twisting or bending in response to forces that may be transmitted during actuation of the drive portion 30 of each of the plurality of sliders 205.

Figure 5:
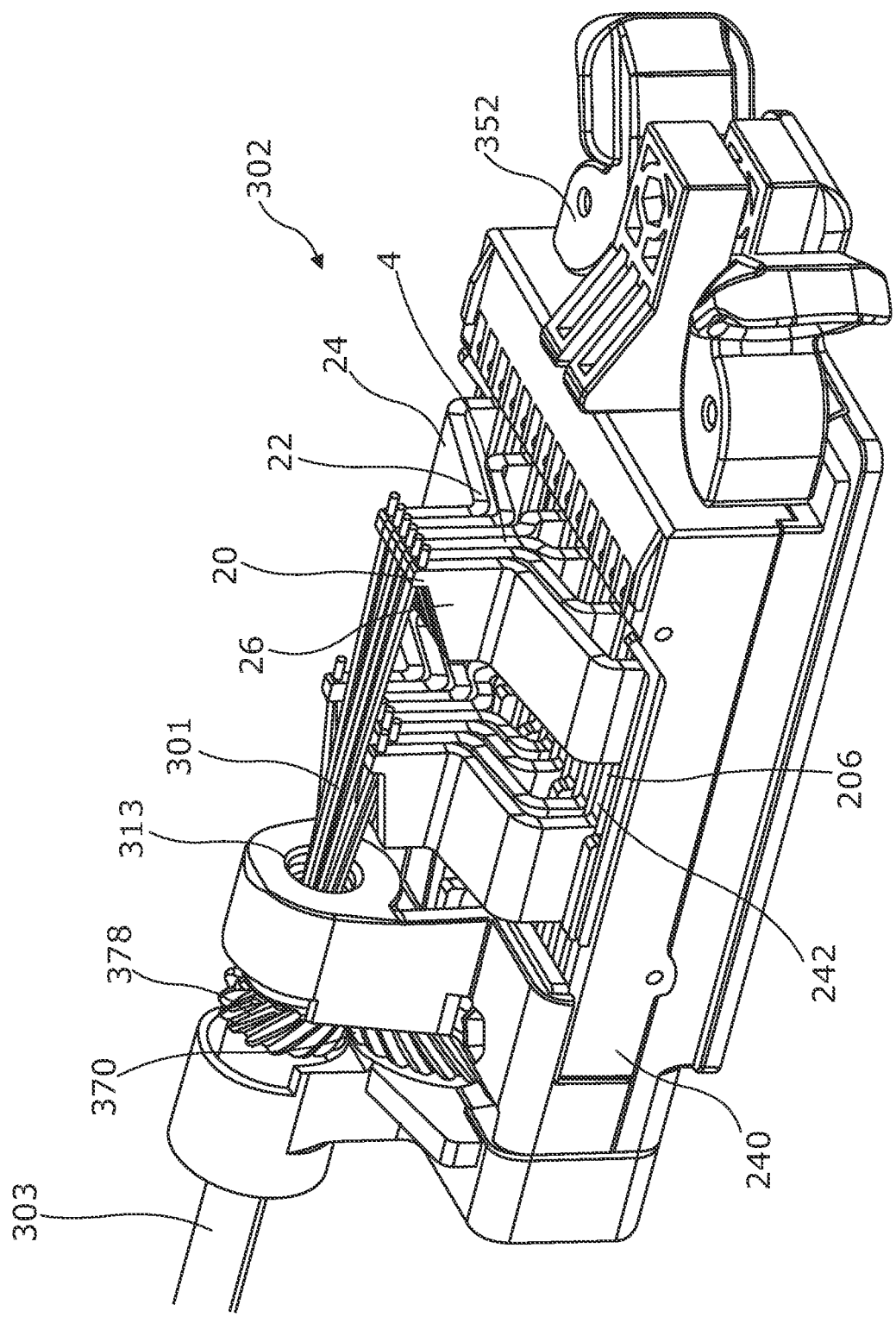
FIG. 5 is an illustration of a driver module according to a further embodiment of the first aspect of the invention comprising a shaft receiving portion, a locking mechanism and a gear mechanism.

Referring now to FIG. 5, a driver module according to another embodiment of the first aspect of the invention is defined generally by the reference numeral 302. The driver module 302 comprises all features of the driver module 202 shown in FIG. 4 and further comprises a plurality of tendons 301, a shaft 303, a shaft receiving portion 313, an attachment interface 350, a locking mechanism 352 and a gear assembly 370.

The gear assembly comprises a geared shaft 378. The shaft receiving portion 313 is adapted to receive the geared shaft 378 such that the geared shaft 378 is rotatably attached to the shaft receiving portion 313. The geared shaft is in turn adapted to receive the shaft 303 such that the shaft 303 is non-rotatably attached to the geared shaft 378.

A plurality of tendons 301 extend through the shaft 303, geared shaft 378 and shaft receiving portion 313. Each of the tendons 301 is received at a first end by a corresponding tendon receiving portion 20.

The alignment portion 24 of each of the plurality of sliders 4 is adapted to position the tendon receiving portions 20 of the sliders 4 into close alignment with one another as described above in relation to FIG. 4. In this embodiment, this also results in the tendon receiving portions 20 being in close axial alignment with the shaft receiving portion. As a result, the tendons 301, which extend through the shaft 303, remain in approximate alignment as they extend out of the shaft receiving portion 313 towards a corresponding tendon receiving portion 20.

The maintenance of the plurality of tendons 301 substantially in alignment with the shaft 303, obviates the need to divert the tendons 301 by use of pulleys or any other means in order to reach a tendon receiving portion. This in turn reduces the number of parts required in the driver module 302 and also reduces the potential for wear of the plurality of tendons 301.

The attachment interface 350 is engageable with a barrier which is in turn engageable with a motor module. The locking mechanism 352 is adapted to lock and unlock the attachment interface 350 into and out of engagement with the barrier respectively.

Figure 6:
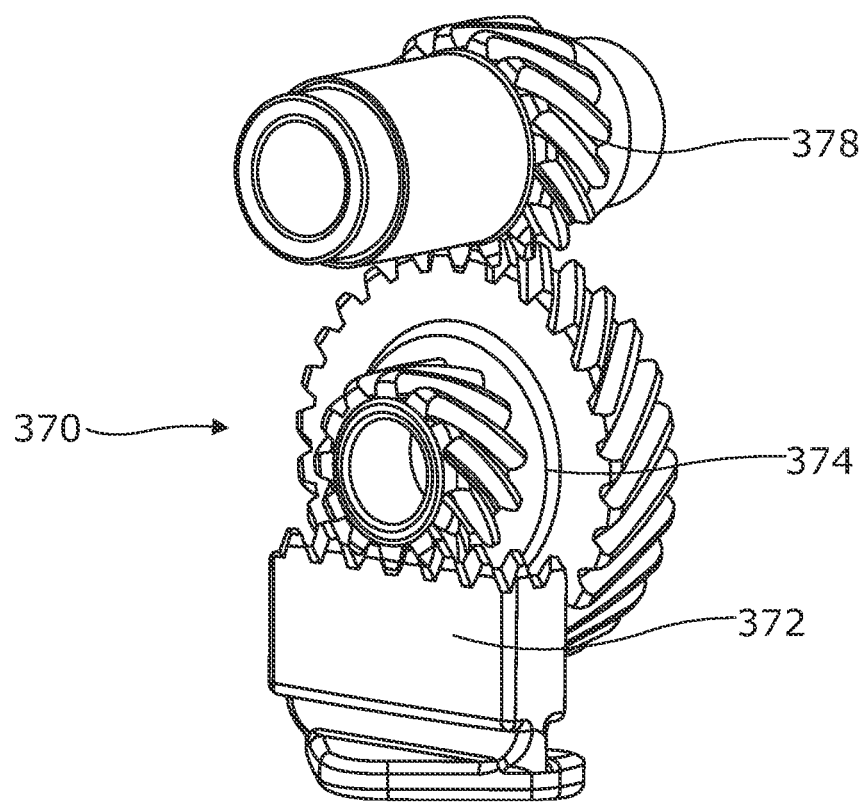
FIG. 6 is an illustration of the gear mechanism shown in FIG. 5, shown here removed from the driver module.

Referring now to FIG. 6, the gear assembly shown in FIG. 5 is shown in more detail. The gear assembly comprises a gear slider 372 and a gear wheel 374. The gear slider 372 is moveable in a linear direction, the gear wheel 374 is rotatable about its central axis and the geared shaft 378 is rotatable about its central axis which it shares with the shaft 303 shown in FIG. 5. The gear slider 372 is engageable with the gear wheel 374 which is in turn engageable with the geared shaft 378. Linear movement of the linear slider 372 drives rotation of the gear wheel 374 about its axis which in turn drives rotation of the geared shaft 378 about its axis. When the shaft 303, shown in FIG. 5, is non-rotatably attached to the geared shaft 378, linear movement of the gear slider 372 drives rotation of the geared shaft 378 about its axis which in turn rotates the shaft 303.

Figure 7:
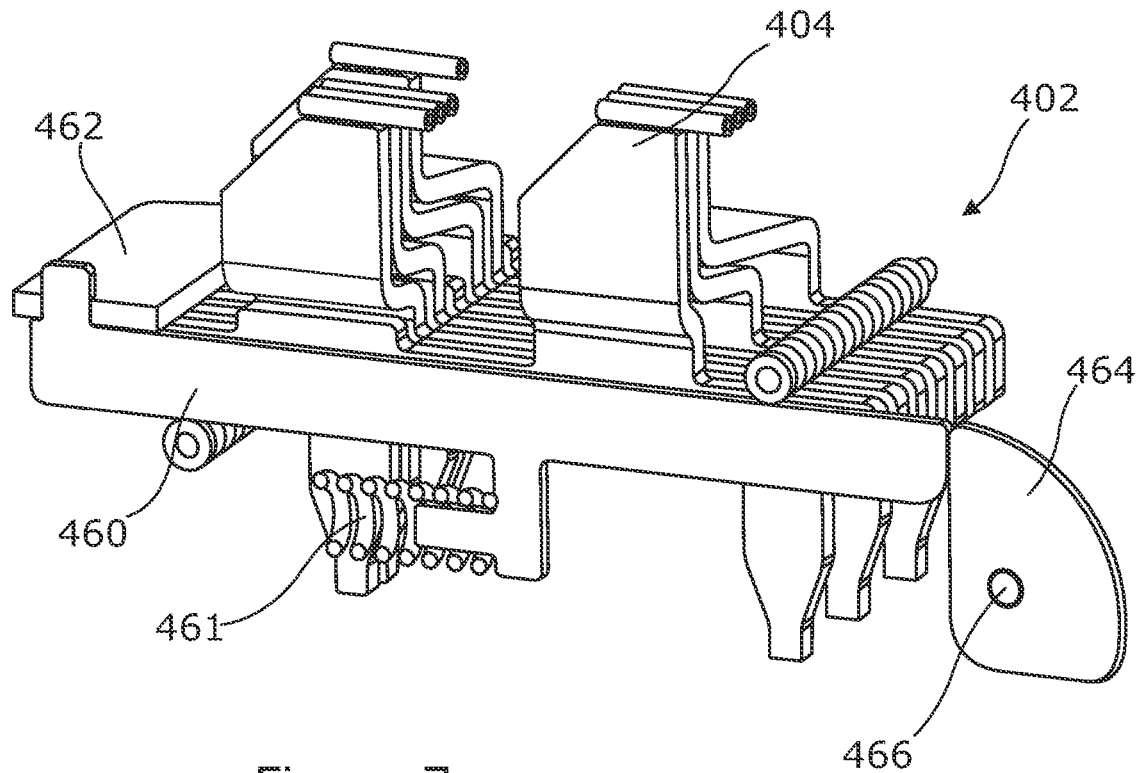
FIG. 7 is a cross-sectional perspective view of a driver module, according to a further embodiment of the first aspect of the invention, comprising a pre-tensioning actuator.

Referring now to FIG. 7, a driver module according to another embodiment of the first aspect of the invention is defined generally by the reference numeral 402. A cross-sectional view of the driver module 402 is shown that comprises a plurality of sliders 404, a pre-tensioning actuator 460 and a disengagement device 464. The pre-tensioning actuator comprises a biasing element 461 and a cross plate 462. The disengagement device 464 comprises a lever pin 466 about which the disengagement device is rotatable. The lever pin may be attached to a guide tray, thereby anchoring the disengagement device in the driver module 402. (The guide tray is not shown here but may be considered as equivalent to the guide trays 40, 140, and 240 shown in FIGS. 2, 3, 4 and 5)

Figure 8:
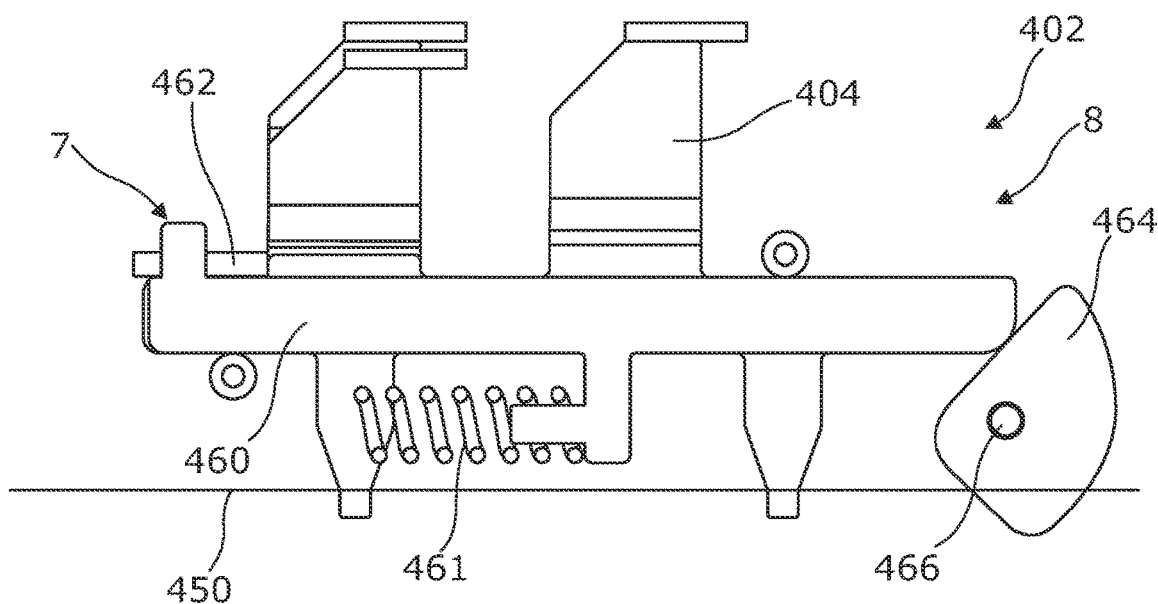
FIG. 8 is an illustration of the driver module shown in FIG. 7, here showing the pre-tensioning actuator in a first position.

Referring now to FIG. 8, a cross-section of the driver module 402 is shown. The pre-tensioning actuator 460 is shown in a first position where it is engaged with the plurality of sliders 404 via the cross plate 462.

The biasing element 461, which in this embodiment of the invention takes the form of a spring. The biasing element biases the pre-tensioning actuator toward the second end 8 of the slider receiving portion (not shown). In moving toward the second end 8 of the slider receiving portion 6, the pre-tensioning actuator 460 comes into contact with, and engages the plurality of sliders 404. The pre-tensioning actuator 460 continues to move toward the second end 8 of the slider receiving portion and in doing so provides movement of the plurality of sliders 404 in the same direction. This continues until a plurality of tendons are in complete tension and the plurality of sliders 5 may move no further. (The plurality of tendons is not shown here but may be considered as equivalent to the plurality of sliders 301 shown in FIG. 5.) Hence the pre-tensioning actuator 460 is provided to maintain the tension of the plurality tendons, which helps to keep the plurality of tendons 401 in good condition.

Figure 9:
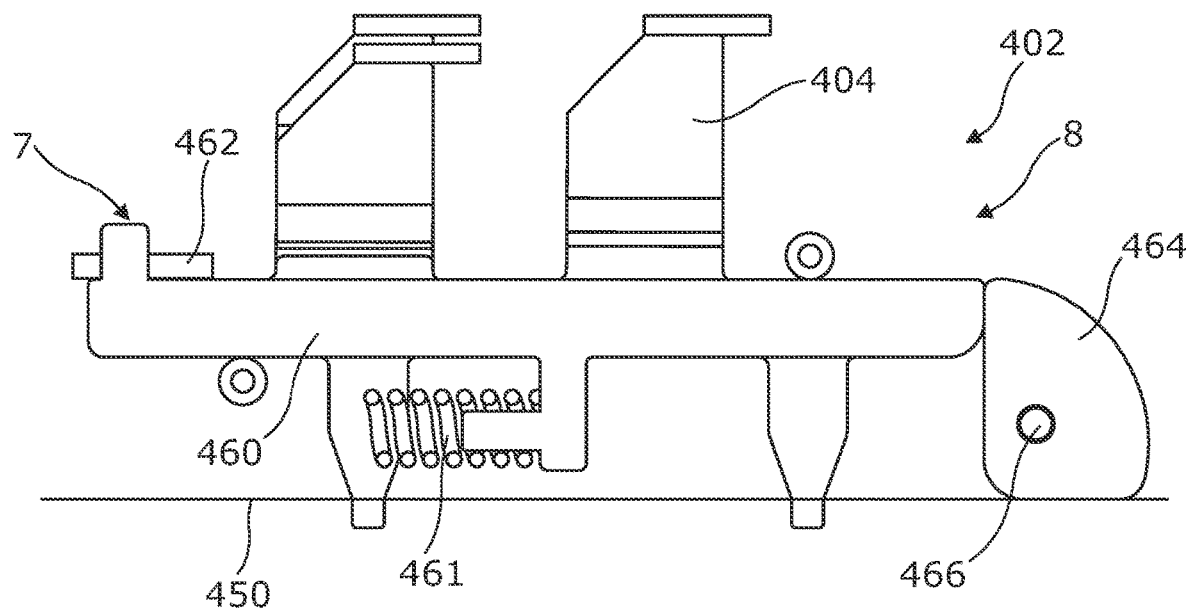
FIG. 9 is an illustration of the driver module shown in FIG. 7, here showing the pre-tensioning actuator in a second position.

Referring now to FIG. 9, a cross-section of the driver module 402 is shown similarly to FIG. 8. The pre-tensioning actuator 460 is shown in a second position where is the cross plate 462 is disengaged with the plurality of sliders 404.

The pre-tensioning device 460 may be moved to the second position by rotating the disengagement device 464 about the lever pin 466 so that it transitions from the position shown in FIG. 8 to that shown in FIG. 9. The rotation of the disengagement device 464 acts against the biasing element 461, in this embodiment by causing compression of the spring. When in the second position, the pre-tensioning device 460, specifically the cross plate 462, is disengaged from the plurality of sliders 404. This provides the plurality of sliders with the ability to move freely in the respective slider channels (not shown), either toward the first end 7 or second end 8 of the slider receiving portion. In this embodiment of the invention the plurality of sliders 404 are able to move 4 mm in either direction when the pre-tensioning actuator 460 is disengaged.

In use, the driver module 402 is engaged with a barrier via an attachment interface 450. The disengagement device 464 in the position shown in FIG. 8 protrudes from the surface of the attachment interface 450 so that, when the driver module 402 is engaged with the barrier, the disengagement device 464 is caused to rotate about the lever pin 466 toward the position shown in FIG. 9. This rotation of the disengagement device 464 results in movement of the pre-tensioning actuator 460 from the first position to the second position, against the bias of the biasing element 461.

This means that, when the driver module 402 is engaged with the barrier, ready for use, the disengagement device 464 automatically disengages the pre-tensioning actuator 460 from the plurality of sliders 404 so that the sliders 404 are free to move without pressure being exerted against them by the biasing element 461.

Figure 10:
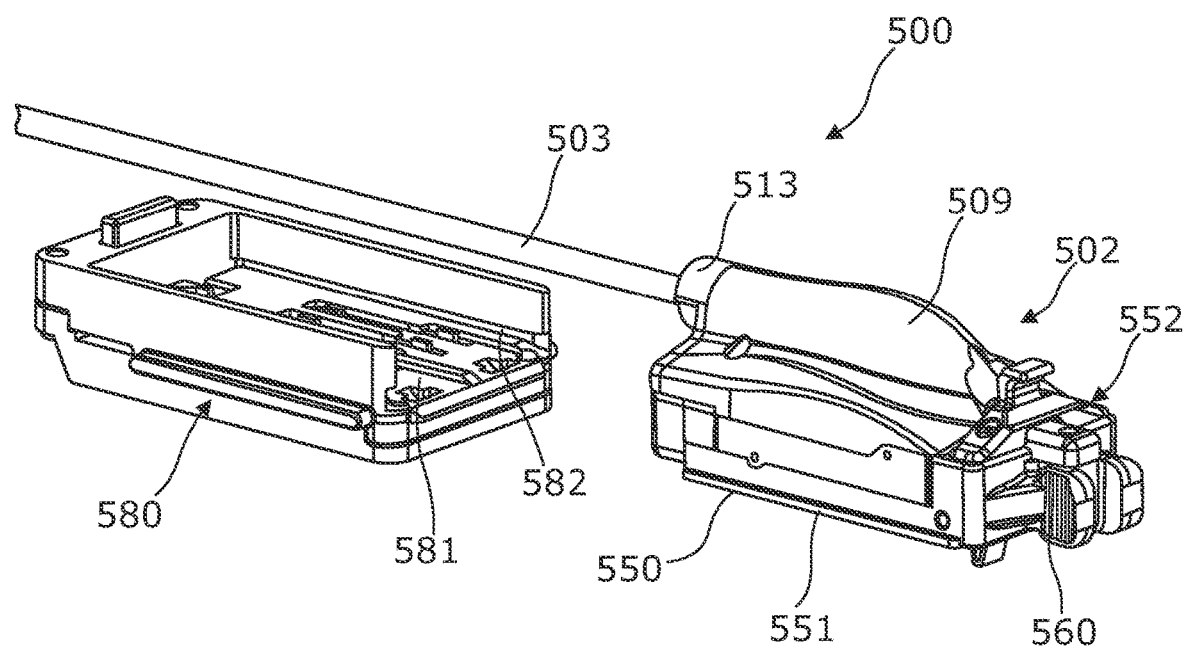
FIG. 10 is an illustration of a driver module, according to a further embodiment of the first aspect of the invention, comprising a locking mechanism similar to that shown in FIG. 5. A barrier according to an embodiment of the second aspect of the invention is also shown.

Referring now to FIG. 10, a surgical instrument according to an embodiment of the second aspect of the invention is defined generally by the reference numeral 500. The surgical instrument comprises a driver module 502, a shaft 503 and a barrier 580.

The driver module 502 comprises an outer casing 590, a shaft receiving portion 513, an attachment interface 550, a locking mechanism 552 and a grip 559, while the barrier 580 comprise a barrier interface 581. The driver module 502 is positioned so that the attachment interface 550 is ready to be engaged with the barrier interface 581 of the barrier. The barrier interface 581 is an example of a mating interface with which the attachment interface 550 may be engaged. The attachment interface 550 may be engaged with any suitable mating interface, another example being a mating interface forming part of a motor module for actuating the sliders of the driver module 502.

The barrier interface 581 comprises a pair of barrier grooves 582 that extend along the length of the barrier interface 581 and the attachment interface 550 comprises a pair of attachment ridges 551 that extend along the length of the attachment interface 550 and that are receivable by the barrier grooves 582. In use, the attachment interface 550 may be engaged with the barrier interface 581 by gripping the grip 559 and simply sliding the attachment interface 550 in contact with the barrier interface 581 such that the attachment ridges 551 are fully received by the barrier grooves 582.

The shaft 503 is engaged with the shaft receiving portion 513.

Figure 11:
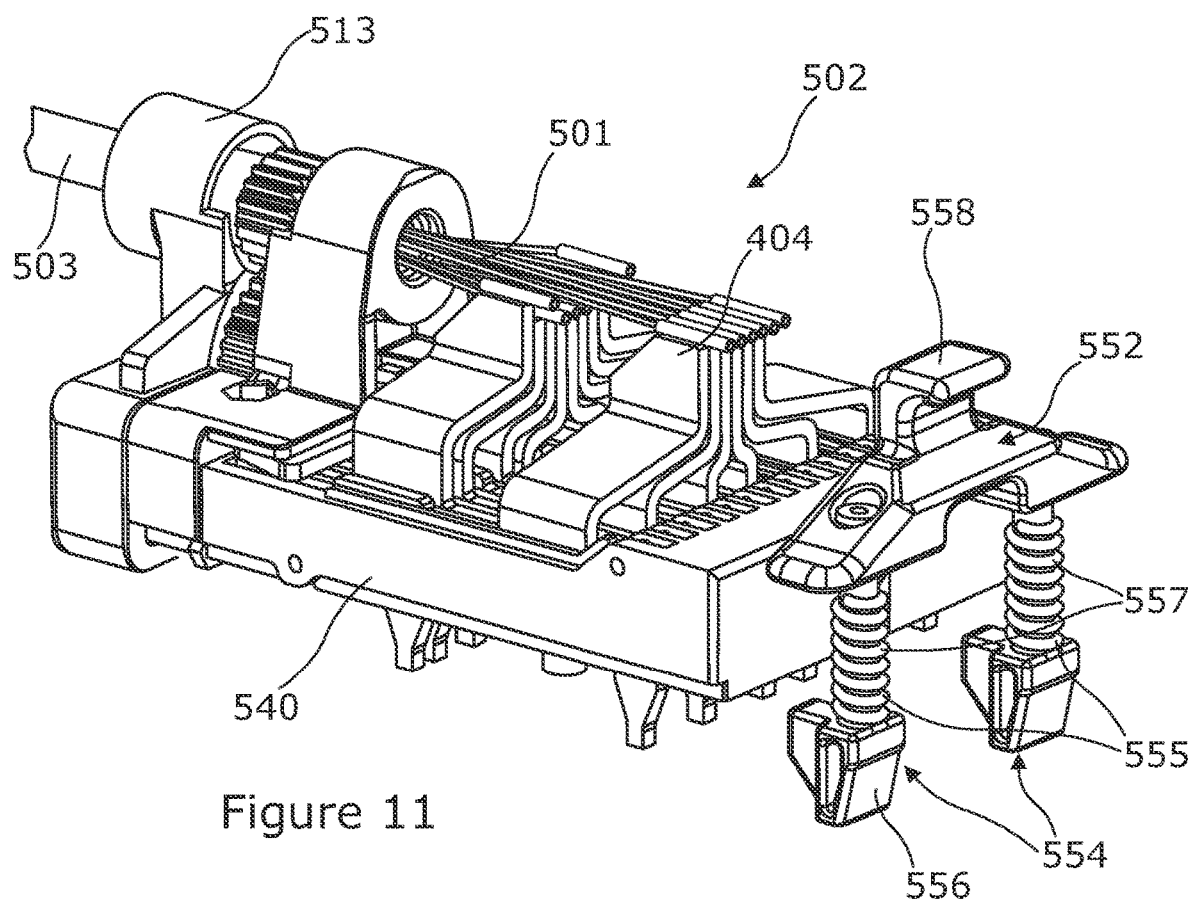
FIG. 11 is an illustration of the driver module shown in FIG. 10 with internal elements of the locking mechanism revealed.

Referring now to FIG. 11, the driver module 502 shown in FIG. 10 is illustrated with the outer casing 590 and the attachment interface 550 removed in order to reveal internal elements of the locking mechanism 552.

In this embodiment of the invention, the locking mechanism 552 comprises a pair of latches 554, a pair of springs 557 and a release handle 558. The pair of latches 554 are spaced apart from one another and extend normally from the release handle 558, parallel to one another. Each latch 554 comprises a piston 555 at a proximal end and a wedge 556 at a distal end. Further, each latch 554 is coupled to the release handle 558 at its proximal end, wherein the piston 555 extends from the release handle 558 shaped as a cylindrical bar which is surrounded by a respective one of the springs 557. The wedge 556, extends further from the piston 555 with a wedge-shape that tapers toward a distal end of the latch 554.

Figure 12:
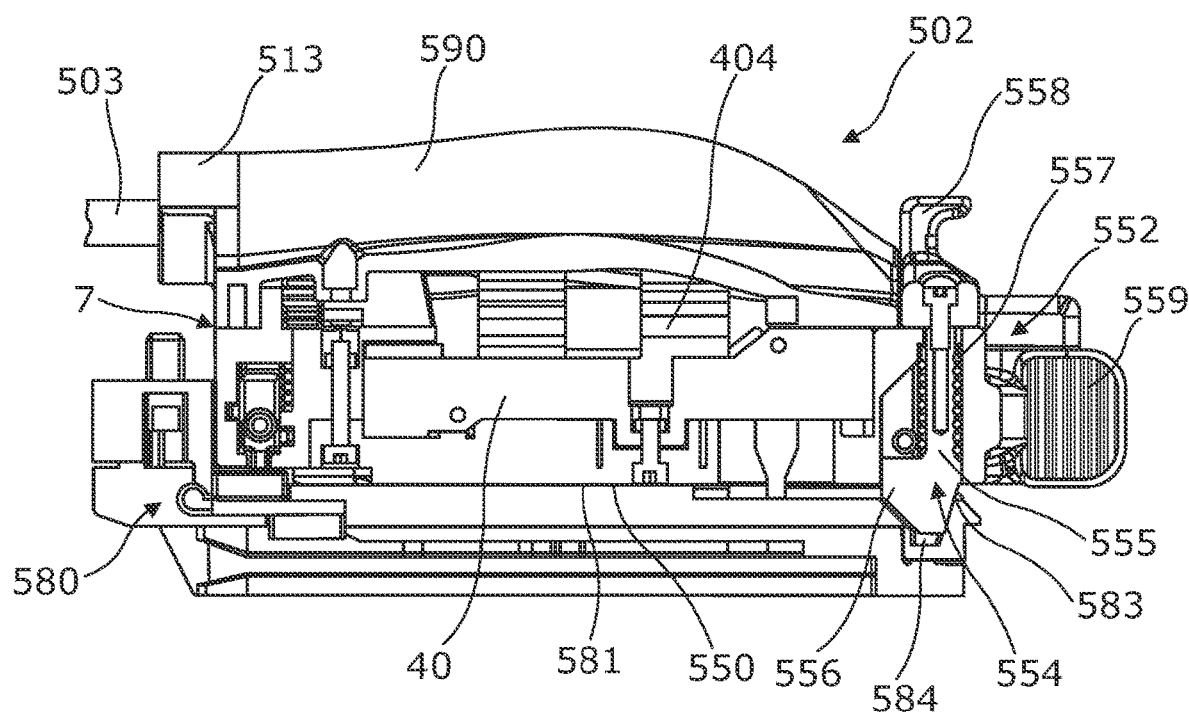
FIG. 12 is a cross-sectional view of the driver module shown in FIG. 10 in engagement with the barrier also shown in FIG. 10.

Referring now to FIG. 12, a cross-sectional view of the driver module 502 and barrier 580 shown in FIG. 10 is provided wherein the driver module 502 is engaged with the barrier 580. Here only a single latch 554 and respective spring 557 are visible though the second latch and spring are still present. Description of the latch 554 and spring 557 shown in FIG. 12 set out below therefore also applies to the latch 554 and spring 557 that are not shown.

The latch 554 and respective spring 557 are encased in the attachment interface 550. A first end of the spring 557 is attached to the latch 554 while a second end is attached to the attachment interface 550. Movement of the latch 554 relative to the attachment interface in the direction of its proximal end causes compression of the spring 557, such that the wedge 556 of the latch 554 is biased by the spring 557 toward protruding from the attachment interface 550.

When engaging the driver module 502 with the barrier 580, the attachment interface 550 is slid over the barrier interface 581 such that the attachment ridges 551 are received by the barrier groove 582 as described above. However, the wedge 556 protrudes from the attachment interface and abuts against a leading edge 583 of the barrier interface 581 when the attachment interface 550 is slid over the barrier interface 581. Hence full receival of the attachment ridges 551 into the barrier grooves is obstructed.

The wedge 556 and the leading edge 583 are adapted such that the leading edge 583 and an abutting surface of the wedge 556 are at a complimentary angle to one another. Once the wedge 556 is in abutment with the leading edge 583, further linear sliding movement of the attachment interface relative to the barrier interface 581 causes the latch to be forced in the direction of its proximal end, normal to the sliding movement and against the bias of the spring 557.

As is shown in FIG. 12, the barrier comprises a latch socket 584 adapted to receive the wedge 556. Therefore, when the attachment interface 550 is slid further over the barrier interface 581 so that the tip of the wedge 556 has passed the leading edge 583, the bias of the compressed spring 557 causes the wedge 556 to move so that it again protrudes from the attachment interface 550 and thereby extends into the latch socket 584. The walls of the latch socket 584 are adapted so that, as the wedge 556 extends into the latch socket 584 due to the bias produced by the spring 557, the attachment interface 550 is pushed further over the barrier interface 581. The attachment interface 550 may continue to slide over the barrier interface 581 in this manner, until each of the plurality of sliders 404 is touching a respective barrier slider (referred to in further detail with respect to FIG. 15).

The movement of the driver module 502 into engagement with the barrier 580 as set out above, and particularly movement of the sliders 404 into engagement with the barrier sliders, may result in stretching tendons attached to the sliders 404 (via the tendon receiving portions 20) until the tensile force in the tendons is balanced with the force introduced by the spring 557. The resulting tensile force in the tendons may increase the robustness of the surgical instrument 500 (particularly an articulated module such as the articulated module 704 shown in FIG. 16) and reduce backlash in the surgical instrument 500 when in use. The wedge 556 and the strength of the spring 557 may be designed to achieve optimal tension in the tendons while risk of the wedge 556 dislodging is prevented when an external force tries to push the driver module 502 away from the barrier 580.

In order to disengage the driver module 502 from the barrier 580, the release handle 558 may be pulled away from the driver module 502, thereby moving the pair of latches 554 against the bias of their respective springs 557 and withdrawing each wedge 556 from its respective latch socket 584. The driver module 502 may then be slid away from the barrier 580 in the reverse direction of that with which it was originally engaged.

Figure 13:
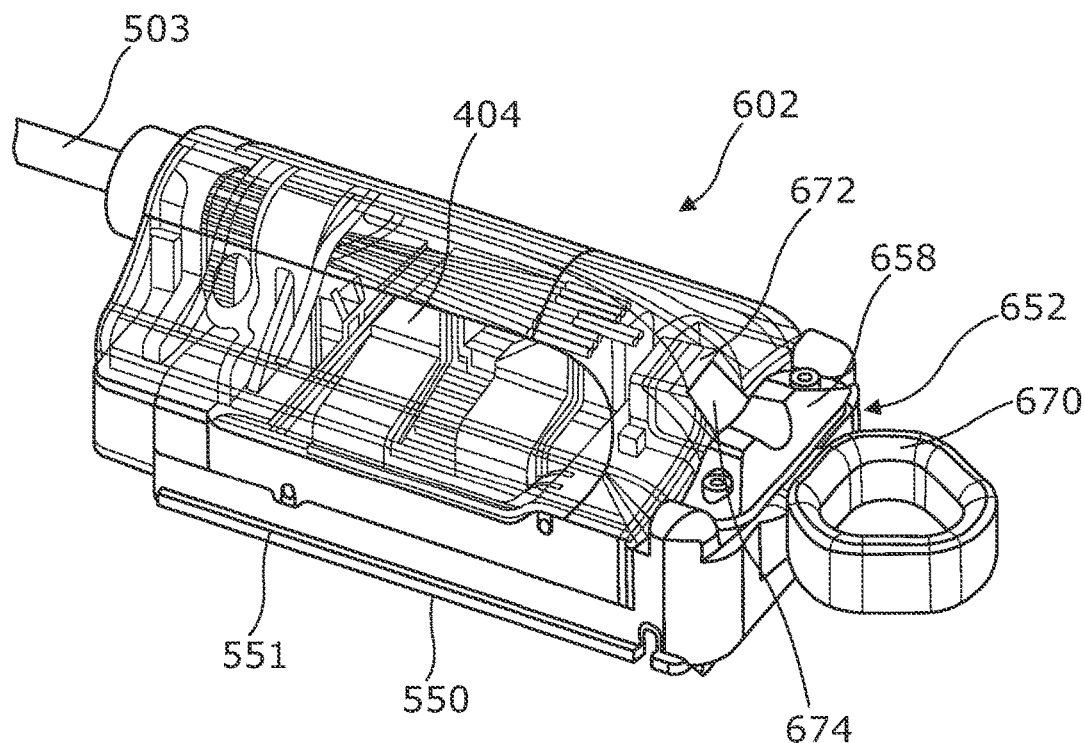
FIG. 13 is illustration of a driver module, according to a further embodiment of the first aspect of the invention comprising a pulling ring.

Referring now to FIG. 13, a driver module 602 according to another embodiment of the first aspect of the invention is similar to the driver module 502 shown in FIGS. 10 to 12 except that it comprises a locking mechanism 652 which differs to the locking mechanism 552. Firstly, the locking mechanism 652 comprises a release bridge 658 rather than the release handle 558. Further, the locking mechanism 652 comprises a moveable pulling ring 670 rather than the static grip 559. Extending from the pulling ring 670, under the release bridge 658 and into the outer casing (which is transparent in FIG. 13) is a bridge actuator 672 which expands in thickness as it extends away from the pulling ring 670. The bridge actuator comprises a sloped surface 674 which is engageable with the release bridge 658 and may cause the release bridge 658 to move relative to the remainder of the driver module 602 depending on the position of the bridge actuator 672. (The other features of the driver module 602, such as the plurality of sliders 404 and the shaft 503, are identical to the driver module 502 shown in FIGS. 10 to 12.)

In use, rather than pulling the release handle 558 to retract the latch 554 (shown in FIGS. 11 and 12), a user may instead pull the pulling ring 670 away from the driver module 602 to cause the bridge actuator 672 to move in the same direction as the pulling ring 670. The sloped surface 674 may thereby be caused to push against the release bridge 658 and, further, cause the release bridge 658 to slide over the bridge actuator 672, hence raising the release bridge 658 away from the driver module 602. As the release bridge 658 is raised, the latch 554 may be retracted into the driver module 602 and the driver module 602 may be disengaged from a barrier (such as the barrier 580 shown in FIGS. 10 and 12), for example.

The pulling ring 670 and bridge actuator 672 may be moveable parallel to the shaft 503 and the attachment interface 550. Therefore, a user may advantageously be able to disengage the driver module 602 from a barrier 580 with a single motion in a single direction, rather than needing to pull a release handle 558 in one direction while pulling the driver module 502 in a different direction.

Figure 14:
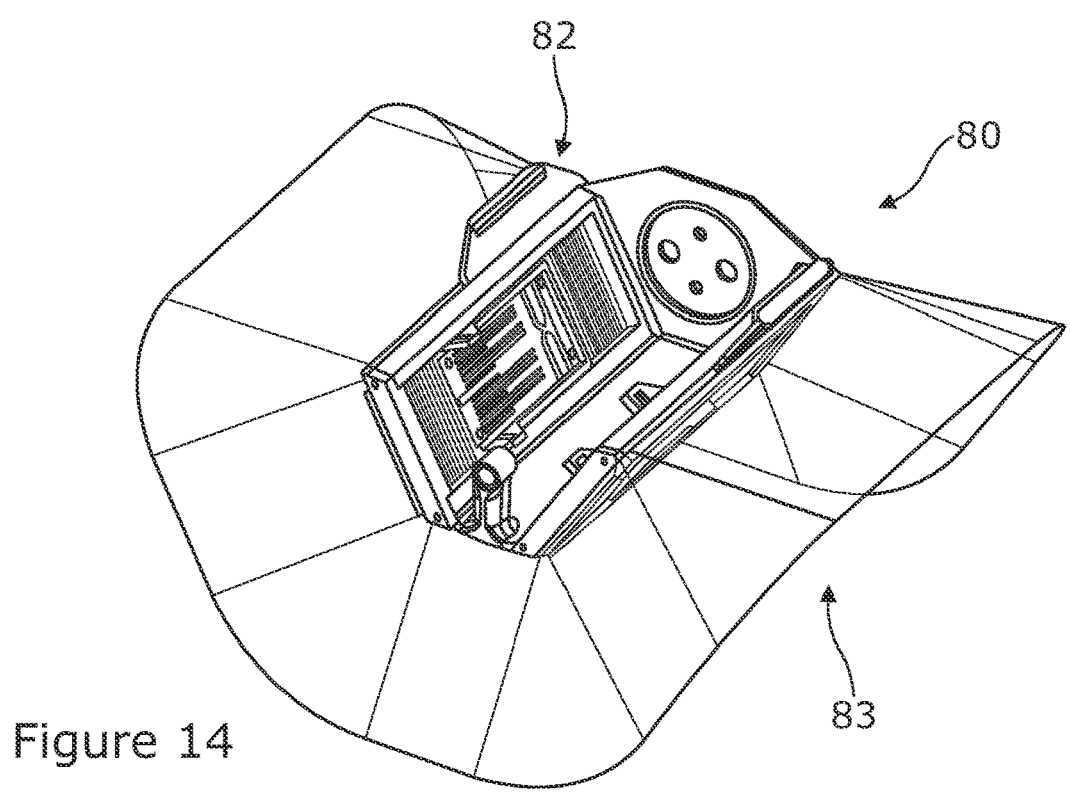
FIG. 14 is an illustration of a barrier according to a further embodiment of the second aspect of the invention.

Referring now to FIG. 14, a barrier according to another embodiment of the second aspect of the invention is defined generally by the reference numeral 80. The barrier comprises a first side 82 and a second side 83. The second side is configured to engage and cover non-sterile items such as a motor module. The first side is configured to engage with sterile items such as the driver module 502 shown in FIG. 10 and protect them from non-sterile items, thus maintaining their sterility. Hence the barrier 80 is provided to form a physical barrier between non-sterile items and sterile items, such as a driver module according to the first aspect of the invention, to ensure the sterile items remain sterile.

Figure 15:
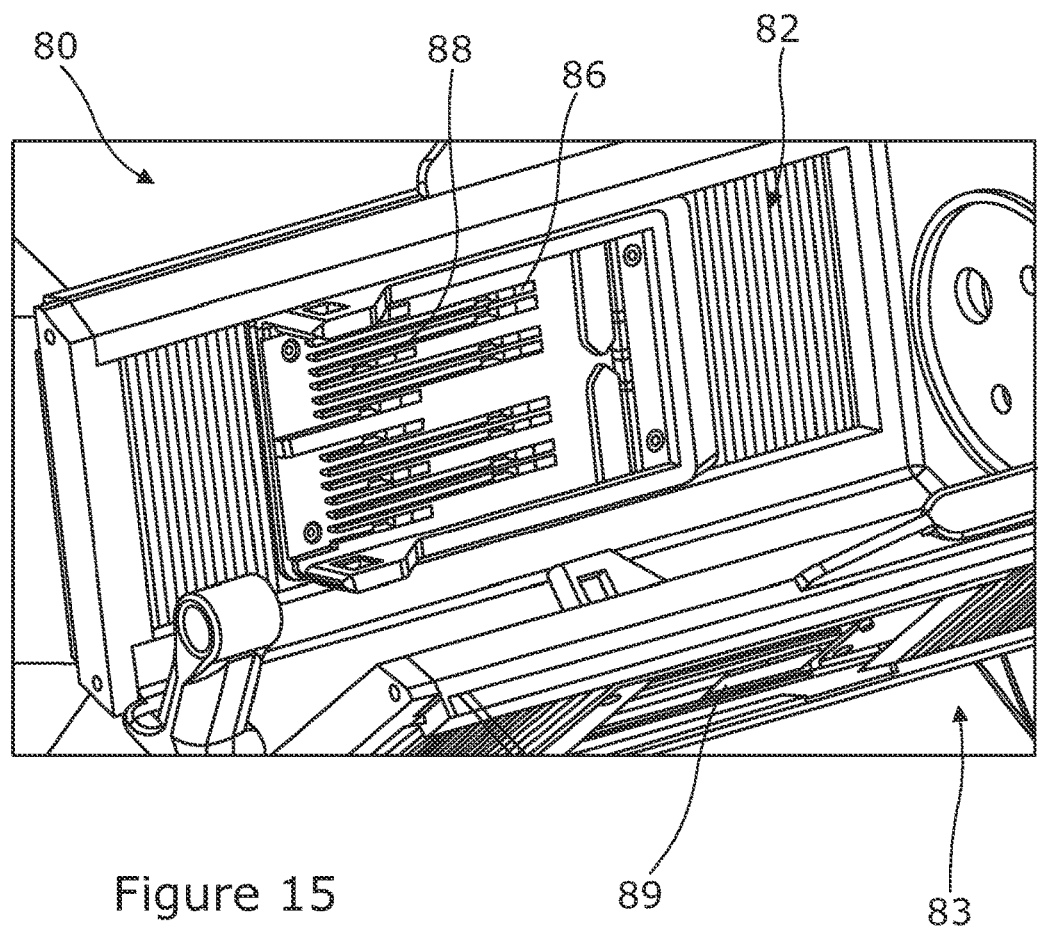
FIG. 15 is an illustration of the barrier shown in FIG. 11, here showing a barrier slider.

Referring now to FIG. 15, an expanded view of the barrier 80, shown in FIG. 12, is provided. The barrier 80 further comprises a plurality of barrier sliders 86, wherein each of the plurality of barrier sliders 86 comprises a first portion 88 and a second portion 89. Each first portion 88 is engageable with a corresponding one of a plurality of sliders 4, 104, 404 that may be provided by a driver module 302, 102, 502 shown in FIGS. 5, 3 and 11 respectively. Each second portion 89 is engageable with one of a plurality of actuators provided by a motor module.

Figure 16:
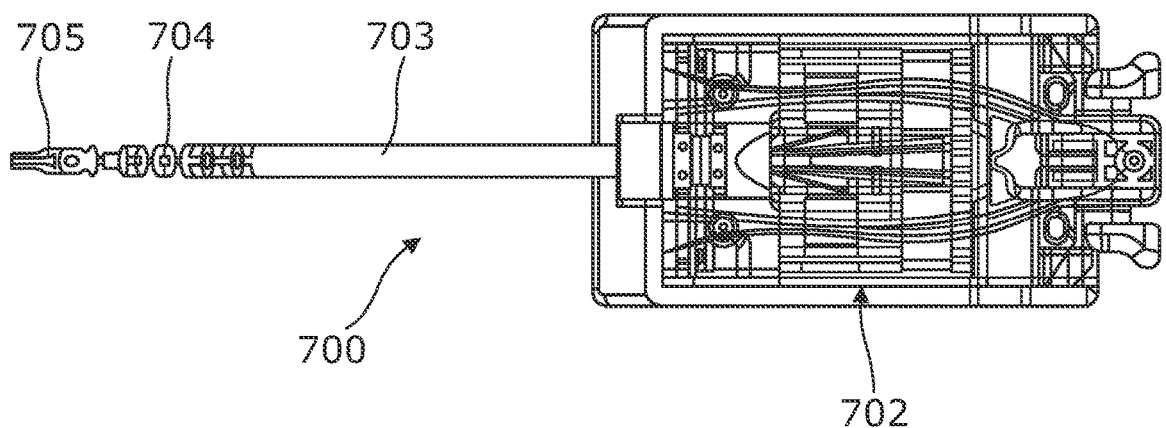
FIG. 16 is an illustration of a surgical instrument according to an embodiment of the second aspect of the invention, comprising a driver module as shown in FIG. 6, a shaft, an articulation module and an end effector.

Referring now to FIG. 16, a surgical instrument according to an embodiment of the second aspect of the invention is defined generally by the reference numeral 700. The surgical instrument 700 comprises a driver module 702 and shaft 703 similar to, and interchangeable with, the driver modules 502, 602 and shafts 503,603 shown in FIGS. 10 and 13. The surgical instrument 700 further comprises an articulation module 704 and an end effector 705. The articulation module 704 is coupled to the shaft 703, whereby the shaft 703 is positioned between the driver module 702 and the articulation module 704. The end effector 705 is coupled to the articulation module 704, whereby the articulation module 704 is positioned between the shaft 703 and the end effector 705.

Figure 17:
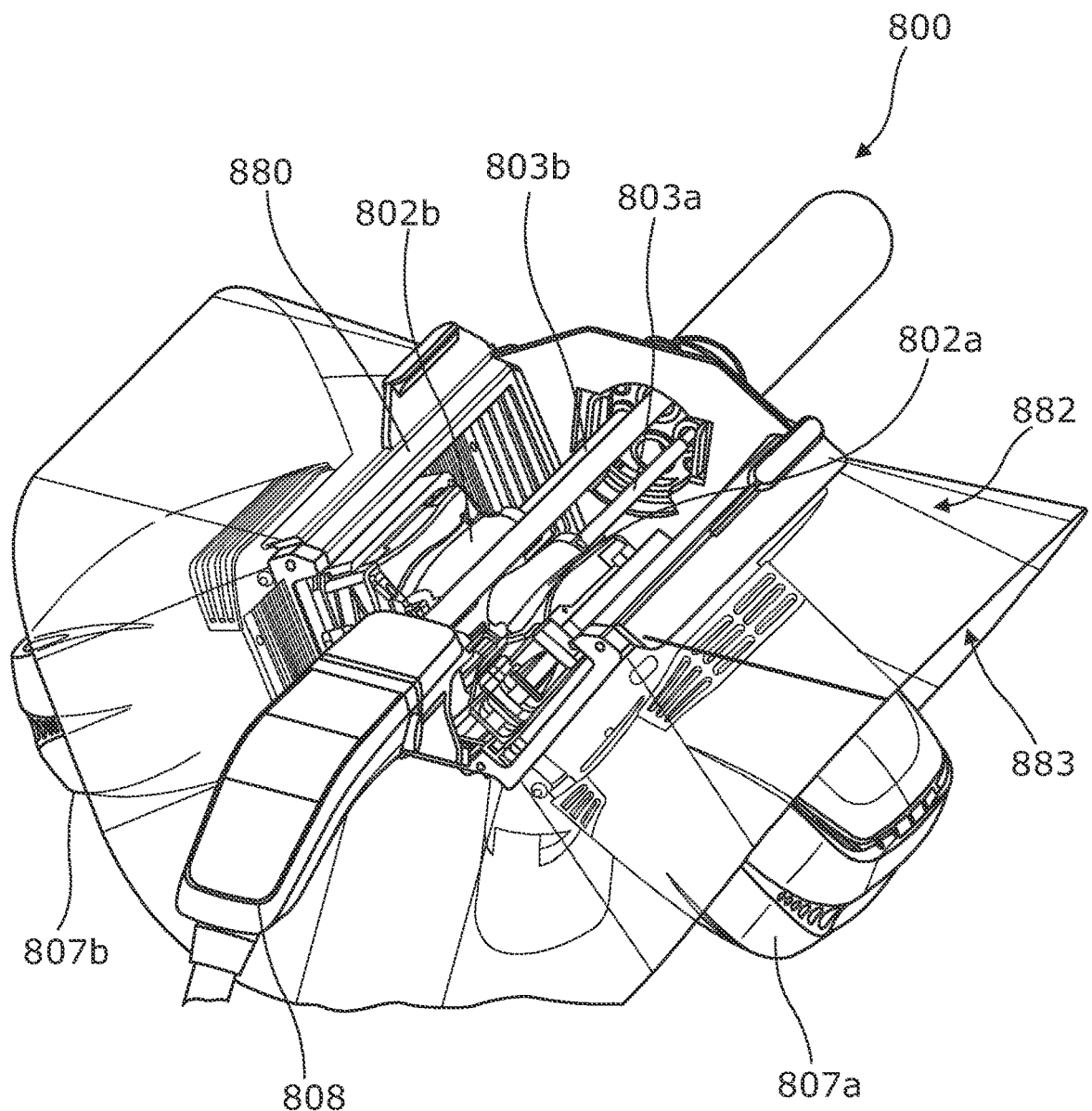
FIG. 17 is an illustration of a surgical instrument according to a further embodiment of the second aspect of the invention, comprising a driver module, a shaft, a barrier and a motor module.

Referring now to FIG. 17, a surgical instrument according to a further embodiment of the second aspect of the invention is defined generally by the reference numeral 800. The surgical instrument comprises a pair of driver modules 802a, 802b and shafts 803a, 803b similar to those shown in FIGS. 10 and 15. The surgical instrument 800 further comprises a pair of motor modules 807a, 807b and a barrier 880, similar to that shown in FIGS. 14 and 15, which comprises a first side 882 and a second side 883. The pair of driver modules 802a, 802b are both engaged with the first side 882 of the barrier 880 and the pair of motor modules are both engaged to the second side 883 of the barrier 880.

Also shown in FIG. 17 is an endoscope 808 which may be used alongside the surgical instrument 800.

The invention claimed is:

1. A driver module for actuating a tendon, the driver module comprising:
   a plurality of sliders, each of the sliders comprising a base portion, a tendon receiving portion and a body portion, the tendon receiving portion being spaced apart from the base portion and the body portion extends from the base portion to the tendon receiving portion,
   the module further comprising a slider receiving portion having a first end and a second end and engageable with the base portion of the slider such that the slider is moveably attachable to the slider receiving portion,
   wherein the body portion of each of the plurality of sliders further comprises an alignment portion, which is adapted to place the tendon receiving portions of the adjacent sliders to abut with or be close to each other.

2. A driver module according to claim 1 further comprising a shaft receiving portion positioned toward the first end of the slider receiving portion, wherein the tendon receiving portion is aligned with the shaft receiving portion.

3. A driver module according to claim 2 wherein the alignment portion being adapted to position the tendon receiving portion of each of the sliders in alignment with the shaft aperture.

4. A driver module according to claim 1, wherein each of the sliders further comprises a drive portion extending from the base portion, such that the base portion is positioned between the body portion and the drive portion.

5. A driver module according to claim 1, wherein the slider receiving portion comprises a plurality of channels spaced apart from one another and extending at least partially along the length of the slider receiving portion between the first end and the second end, each of the channels being adapted to receive the base portion of one of the sliders, whereby the base portion is slideably moveable within the channel.

6. A driver module according to claim 1 further comprising a first roller having an axis and configured to be axially rotatable, the first roller being positionable such that the axis of the first roller is normal to the base portion of the slider and engageable with the base portion of each of the sliders such that movement of the sliders causes axial rotation of the first roller.

7. A driver module according to claim 6 further comprising a second roller having an axis and configured to be axially rotatable, the first and second rollers being spaced apart from one another, the first roller being engageable with a first side of the base portion and the second roller being engageable with a second side of the base portion.

8. A driver module for actuating a tendon, the driver module comprising:
   a slider comprising a base portion, a tendon receiving portion and a body portion, the tendon receiving portion being spaced apart from the base portion and the body portion extends from the base portion to the tendon receiving portion;
   the module further comprising a slider receiving portion having a first end and a second end and engageable with the base portion of the slider such that the slider is moveably attachable to the slider receiving portion; and
   a pre-tensioning actuator, the pre-tensioning actuator being moveable between a first position and a second position, wherein in the first position the pre-tensioning actuator is engaged with the slider such that the slider is positioned toward the second end of the slider receiving portion, and in the second position the pre-tensioning actuator is disengaged from the slider; the driver module further comprises a bias, biasing the pre-tensioning actuator towards the first position.

9. A driver module according to claim 8, the driver module further comprising a deactivating device engageable with the pre-tensioning actuator and moveable to a deactivating position wherein the pre-tensioning actuator is configured in its second position.

10. A driver module according to claim 1, wherein the body portion of each slider comprises a head portion positioned such that the head portion of that slider is abuttable with the head portion of at least one other adjacent slider.

11. A driver module according to claim 1, the driver module further comprising an attachment interface and a locking mechanism, the attachment interface being engageable with a mating interface, the locking mechanism being adapted to lock and unlock the attachment interface in engagement with the mating interface.

12. A driver module according to claim 11, wherein the locking mechanism comprises a latch comprising a wedge, which latch is moveable between a first position in which the wedge is received within the attachment interface, and a second position in which the wedge protrudes from the attachment interface, wherein the latch is biased towards the second position.

13. A driver module according to claim 1, the driver module further comprising a gear assembly, the gear assembly comprising a gear slider moveable in a linear direction, a gear wheel rotatable about a gear axis and a geared shaft rotatable about a shaft axis; the gear slider being engageable with the gear wheel, and the gear wheel being engageable with the geared shaft such that linear movement of the linear slider drives rotation of the gear wheel about the gear axis, whereby the geared shaft rotates about the shaft axis.

14. A surgical instrument comprising:
a driver module according to claim 1,
a plurality of tendons, each of the tendons receivable at a first end by the tendon receiving portion of one of the plurality of the sliders;
an articulation module, operably connectable to the tendon;
a shaft extending from the driver module to the articulation module, wherein the plurality of tendons extend through the shaft;
an end effector, operably connected to one or more of the plurality of the tendons; and
a motor module, comprising an actuator, which actuator is operatively engageable with the plurality of the sliders such that movement of the actuator causes movement of the sliders.

15. A surgical instrument comprising:
a driver module according to claim 1 comprising:
a plurality of tendons, each of the tendons being receivably attached at a first end by the tendon receiving portion of one of the plurality of sliders;
a shaft extending from the driver module, the plurality of tendons extending through the shaft;
an articulation module operatively coupled to the shaft, and attachable to one or more of the plurality of tendons at the second end thereof;
an end effector operatively coupled to the articulation module, and attachable to one or more of the plurality of tendons at a second end thereof; and
a motor module comprising a plurality of actuators, each of the actuators being moveable and engageable with the plurality of sliders such that movement of the actuators provides movement of respective ones of the plurality of sliders.

16. A surgical instrument according to claim 15, the surgical instrument further comprising a barrier having a first side and a second side, the first side being engageable with the driver module and the second side being engageable with the motor module.

17. A surgical instrument according to claim 16, wherein the barrier comprises a plurality of barrier sliders, each of which barrier sliders comprises a first portion and a second portion, the first portion being engageable with one of the plurality of sliders of the driver module and the second portion being engageable with one of the plurality of actuators of the motor module.

18. A surgical instrument according to claim 17, wherein:
(a) the driver module is a driver module comprising: a slider comprising a base portion, a tendon receiving portion and a body portion, the tendon receiving portion being spaced apart from the base portion and the body portion extends from the base portion to the tendon receiving portion, the module further comprising a slider receiving portion having a first end and a second end and engageable with the base portion of the slider such that the slider is moveably attachable to the slider receiving portion, the driver module further comprising an attachment interface and a locking mechanism, the attachment interface being engageable with a mating interface, the locking mechanism being adapted to lock and unlock the attachment interface in engagement with the mating interface, wherein the locking mechanism comprise a latch comprising a wedge, which latch is moveable between a first position in which the wedge is received within the attachment interface, and a second position in which the wedge protrudes from the attachment interface, wherein the latch is biased towards the second position,
(b) the mating interface is a barrier interface forming part of the first side of the barrier and comprises a latch socket in which the wedge is receivable when the attachment interface is engaged with the barrier interface, and
(c) the wedge is adapted such that, when the attachment interface is engaged with the barrier interface, the bias of the latch towards the second position causes the driver.

* * * * *